US009862697B2

(12) United States Patent
Glass et al.

(10) Patent No.: US 9,862,697 B2
(45) Date of Patent: Jan. 9, 2018

(54) PH-SENSITIVE FLUORESCENT SENSORS FOR BIOLOGICAL AMINES

(71) Applicant: The Curators of the University of Missouri, Columbia, MO (US)

(72) Inventors: Timothy E Glass, Columbia, MO (US); Kevin D Gillis, Columbia, MO (US); Kenneth S Hettie, Columbia, MO (US); Jessica L Klockow, Columbia, MO (US)

(73) Assignee: The Curators of the University of Missouri, Columbia, MO (US)

(*) Notice: Subject to any disclaimer, the term of this patent is extended or adjusted under 35 U.S.C. 154(b) by 0 days.

(21) Appl. No.: 14/449,672

(22) Filed: Aug. 1, 2014

(65) Prior Publication Data

US 2015/0037811 A1    Feb. 5, 2015

Related U.S. Application Data

(60) Provisional application No. 61/958,610, filed on Aug. 1, 2013.

(51) Int. Cl.
   *C07D 311/16*    (2006.01)
   *G01N 33/74*    (2006.01)

(52) U.S. Cl.
   CPC ........... *C07D 311/16* (2013.01); *G01N 33/74* (2013.01)

(58) Field of Classification Search
   CPC .................. G01N 33/582; G01N 33/74
   See application file for complete search history.

(56) References Cited

U.S. PATENT DOCUMENTS

| | | | |
|---|---|---|---|
| 7,977,120 B2* | 7/2011 | Glass | C07D 215/38 436/106 |
| 2010/0004233 A1* | 1/2010 | Iikura | C07D 311/18 514/230.5 |

OTHER PUBLICATIONS

Feuster et al., "Detection of Amines and Unprotected Amino Acids in Aqueous Conditions by Formation of Highly Fluorescent Iminium Ions", J. Am. Chem. Soc, vol. 125, pp. 16174-16175, published 2003.*
Wolfbeis et al., Synthesis and spectral properties of 7-(N-arylsulfonyl) aminocoumarins, a new class of fluorescent pH indicators, vol. 22, issue 5, pp. 1215-1218, published Apr. 6, 2009.*
Wolfbeis et al., Synthesis and spectral properties of 7-(N-arylsulfonyl) aminocoumarins, a new class of fluorescent pH indicators, vol. 22, issue 5, pp. 1215-1218, published online Apr. 6, 2009.*
Boyd et al., "Trace-Level Amino Acid Analysis by Capillary Liquid Chromatography and Application to in Vivo Microdialysis Sampling with 10-s Temporal Resolution", Analytical Chemistry, 2000, pp. 885-871, vol. 72.

(Continued)

*Primary Examiner* — Tracy Vivlemore
*Assistant Examiner* — Nam P Nguyen
(74) *Attorney, Agent, or Firm* — Thompson Coburn LLP; Steven M. Ritchey

(57) ABSTRACT

The invention is directed to dual-analyte fluorescent chemosensors for the direct detection and visualization (imaging) of neurotransmitters released upon exocytosis. The inventive sensor exploits the high concentration of neurotransmitters (e.g., glutamate, norepinephrine, and dopamine) and capitalizes upon the pH gradient between the vesicle and synaptic cleft.

7 Claims, 4 Drawing Sheets

(56) References Cited

OTHER PUBLICATIONS

Burchfield et al., "Exocytotic Vesicle Behaviour Assessed by Total Internal Reflection Fluorescence Microscopy", Traffic, 2010, pp. 429-439, vol. 11.

Chang et al., "Determination of Catecholamines in Single Adrenal Medullary Cells by Capillary Electrophoresis and Laser-Induced Native Fluorescence", Analytical Chemistry, 1995, pp. 1079-1083, vol. 67.

Deng et al., "Determination of Amino Acid Neurotransmitters in Human Cerebrospinal Fluid and Saliva by Capillary Electrophoresis with Laser-Induced Fluorescence Detection", Journal of Separation Science, 2008, pp. 3088-3097, vol. 31.

Felmy, "Modulation of Cargo Release from dense Core Granules by Size and Actin Network", Traffic, 2007, pp. 983-997, vol. 8.

Ge et al., "Bioanalytical Tools for Single-Cell Study of Exocytosis", Analytical and Bioanalytical Chemistry, 2010, pp. 3281-3304, vol. 397.

Gubernator et al., "Fluorescent False Neurotransmitters Visualize Dopamine Release from Individual Presynaptic Terminals", Science, Jun. 12, 2009, pp. 1441-1444, vol. 324.

Hires et al., "Optical Measurement of Synaptic Glutamate Spillover and Reuptake by Linker Optimized Glutamate-Sensitive Fluorescent Reporters", Proceedings of the National Academy of Sciences, Mar. 18, 2008, pp. 4411-4416, vol. 105 No. 11.

Kennedy et al., "Microcolumn Separations and the Analysis of Single Cells", Science, Oct. 6, 1989, pp. 57-63, vol. 246.

Kristensen et al., "Capillary Electrophoresis of Single Cells: Observation of Two Compartments of Neurotransmitter Vesicles", Journal of Neuroscience Methods, 1994, pp. 183-188, vol. 51.

Leszczyszyn et al., "Nicotinic Receptor-Mediated Catecholamine Secretion from Individual Chromaffin Cells", The Journal of Biological Chemistry, Sep. 5, 1990, pp. 14736-14737, vol. 265 No. 25.

Li et al., "Single-Cell MALDI: A New Tool for Direct Peptide Profiling", Tibtech—Focus, Apr. 2000, pp. 151-160, vol. 18.

Miesenbock et al., "Visualizing Secretion and Synaptic Transmission with pH-Sensitive Green Fluorescent Proteins", Nature, Jul. 9, 1998, pp. 192-195, vol. 394.

Omiatek et al., "Only a Fraction of Quantal Content is Released During Exocytosis as Revealed by Electrochemical Cytometry of Secretory Vesicles", ACS Chemical Neuroscience, 2010, pp. 234-245, vol. 1.

Ponchon et al., "Normal Pulse Polarography with Carbon Fiber Electrodes for In Vitro and In Vivo Determination of Catecholamines", Analytical Chemistry, Aug. 1979, pp. 1483-1486, vol. 51 No. 9.

Rodriguez et al., "Fluorescent Dopamine Tracer Resolves Individual Dopaminergic Synapses and their Activity in the Brain", Proceedings of the National Academy of Sciences, Jan. 15, 2013, pp. 870-875, vol. 110 No. 3.

Steyer et al., "Transport, Docking and Exocytosis of Single Secretory Granules in Live Chromaffin Cells", Nature, Jul. 31, 1997, pp. 474-478, vol. 388.

Klockow et al., Tunable Molecular Logic Gates Designed for Imaging Released Newurotransmitters, Chemistry A European Journal, 2015, pp. 11446-11451, vol. 21.

* cited by examiner

PH-SENSITIVE FLUORESCENT SENSORS FOR BIOLOGICAL AMINES

CROSS-REFERENCE TO RELATED APPLICATIONS

This application claims the benefit of provisional application, U.S. Ser. No. 61/958,610, filed Aug. 1, 2013, which is incorporated herein by reference in its entirety.

STATEMENT REGARDING FEDERALLY SPONSORED RESEARCH OR DEVELOPMENT

This invention was made with Government support under Grant No. CHE-1112194 awarded by the National Science Foundation. The Government has certain rights in the invention.

FIELD OF THE INVENTION

The present invention relates to fluorescent sensors for intracellular analyte detection. More particularly, the present invention relates to fluorescent sensors for detecting and imaging neurotransmitters upon exocytosis.

BACKGROUND OF THE INVENTION

Neurotransmitters are critical to the regulation of the central and peripheral nervous systems and command a number of functions such as learning, memory, sleep, and movement. Deng et al., *Determination of amino acid neurotransmitters in human cerebrospinal fluid and saliva by capillary electrophoresis with laser-induced fluorescence detection*, J. Sep. Sci. 2008, 31, 3088-3097; Boyd et al. *Trace-level amino acid analysis by capillary liquid chromatography and application to in vivo microdialysis sampling with 10-s temporal resolution*, Anal. Chem. 2000, 72, 865-871. Discerning the machinery involved in vesicular fusion, the spatiotemporal mechanisms of synaptic release, and the chemical activity of neurotransmitters is vital to understanding both normal and atypical cellular processes. The ability to effectively monitor exocytotic operations bolsters research in neuroscience, serving as a useful tool in the study of neurophysiology and neuropsychiatric disorders. Methods to evaluate exocytosis include fluorescence imaging, capillary electrophoresis, microelectrochemistry, and mass spectrometry. Gubernator et al., *Fluorescent false neurotransmitters visualize dopamine release from individual presynaptic terminals*, Science 2009, 324, 1441-1444; Steyer et al. *Transport, docking and exocytosis of single secretory granules in live chromaffin cells*, Nature 1997, 388, 474-478; Miesenböck et al., *Visualizing secretion and synaptic transmission with pH-sensitive green fluorescent proteins*, Nature 1998, 394, 192-195; Felmy, *Modulation of cargo release from dense core granules by size and actin network*, Traffic 2007, 8, 983-997; Burchfield et al., *Exocytotic vesicle behavior assessed by total internal reflection fluorescence microscopy*, Traffic 2010, 11, 429-439; Kennedy et al., *Microcolumn separations and the analysis of single cells*, Science 1989, 246, 57-63; Kristensen et al., *Capillary electrophoresis of single cells: observation of two compartments of neurotransmitter vesicles*, J. Neurosci. Meth. 1994, 51, 183-188; Chang et al., *Determination of catecholamines in single adrenal medullary cells by capillary electrophoresis and laser-induced native fluorescence*, Anal. Chem. 1995, 67, 1079-1083; Omiatek et al., *Only a fraction of quantal content is released during exocytosis as revealed by electrochemical cytometry of secretory vesicles*, ACS Chem. Neurosci. 2010, 1, 234-245; Ponchon et al., *Normal pulse polarography with carbon fiber electrodes for in vitro and in vivo determination of catecholamines*, Anal. Chem. 1979, 51, 1483-1486; Leszcezyszyn et al., *Nicotinic receptor-mediated catecholamine secretion from individual chromaffin cells*, Chemical evidence for exocytosis, J. Biol. Chem. 1990, 265, 14736-14737; Li et al., *Single-cell MALDI: a new tool for direct peptide profiling*, Trends Biotechnol. 2000, 18, 151-160. Non-optical techniques are limited by poor throughput and a lack of spatial resolution. Ge et al., *Bioanalytical tools for single-cell study of exocytosis*, Anal. Bioanal. Chem. 2010, 397, 3281-3304. Conversely, fluorescence methods offer a sensitive means to elucidate the spatial distribution of neuronal vesicles and chemical messengers.

Fluorescence imaging of secretion was studied early on by loading chromaffin cells with acridine orange and observing a loss in fluorescence upon exocytosis. Steyer et al., *Transport, docking and exocytosis of single secretory granules in live chromaffin cells*, Nature 1997, 388, 474-478. More recently, exocytosis has been visualized using the genetically-encoded synapto-pHluorins, wherein a pH-sensitive GFP construct is expressed on the inner membrane of secretory vesicles. The engineered vesicles fluoresce upon exocytosis due to a change in pH from the acidic synaptic vesicle (~5) to the neutral synaptic cleft (~7.4). Miesenböck et al., *Visualizing secretion and synaptic transmission with pH-sensitive green fluorescent proteins*, Nature 1998, 394, 192-195. These methods solely monitor the process of vesicle membrane fusion during an exocytotic event but do not directly image active neurotransmitters released upon exocytosis. In recent years, a genetically-encoded CFP/YFP FRET biosensor was developed to monitor glutamate release, spillover, and reuptake by fluorescence. Hires et al., *Optical measurement of synaptic glutamate spillover and reuptake by linker optimized glutamate-sensitive fluorescent reporters*, P. Natl. Acad. Sci. 2008, 105, 4411-4416. However, these protein-based biosensors require genetic manipulation and display high, irreversible affinity for glutamate with limited dynamic range and overall small changes in fluorescence. As a result, these protein-based sensors are neither intended for, nor compatible with, specialized neurosecretory cells (e.g., glutamatergic, dopaminergic, etc.) that possess high concentrations of primary amine neurotransmitters (300 mM-1M). To avoid the use of protein-based fluorophores, a pH sensitive fluorescent false neurotransmitter (FFN) has been developed to monitor exocytosis. More specifically, FFNs solely monitor vesicular membrane fusion with the cellular membrane. This fluorescent tracer is loaded into vesicles expressing VMAT and fluoresces upon exocytosis similar to the synapto-pHluorins. Rodriguez et al., *Fluorescent dopamine tracer resolves individual dopaminergic synapses and their activity in the brain*, P. Natl. Acad. Sci. 2013, 110, 870-875. FFNs neither directly detect neurotransmitters nor directly monitor exocytotic release of neurotransmitters. There remains, however, a scarcity of small molecular sensors that can directly detect and image neurotransmitters upon exocytosis.

In recent years, coumarin aldehyde fluorescent sensors, such as the ones disclosed in U.S. Pat. No. 7,977,120 and International Application No. PCT/US2014/31490, were developed. Both the '120 sensor and the 31490 sensor, with the exemplary structures shown in FIG. 1, are fluorescent sensors for the selective recognition and sensing of amines. The '120 sensor with a boronic acid recognition unit, unfortunately, can be quenched by the catechol group upon binding, and thus, in the case of dopamine and norepinephrine, operated in a turn-off mode. The 31490 sensor is a turn-on sensor for the selective labeling and imaging of the dopamine and norepinephrine inside secretory vesicles. More specifically, the 31490 sensor enters the vesicle and binds to the primary amine of the catecholamine, creating a positively charged iminium ion. Formation of the iminium ion also induces a bathochromic shift in absorbance that can be selectively excited at 488 nm allowing the neurotransmitter to be imaged directly, giving the signature punctate fluorescence. Nettie et al., *Selective catecholamine recognition with NeuroSensor 521: a fluorescent sensor for the visualization of norepinephrine in fixed and live cells*, ACS Chem. Neurosci. 2013, 4, 918-923. The charged complex cannot translocate across the vesicular membrane and becomes trapped, accumulating inside the vesicle and selectively labeling only primary amine neurotransmitters present in high concentrations (50 mM-1M) within an acidic environment (e.g., secretory vesicle).

Therefore, there is a need for new pH-sensitive fluorescent chemosensors that directly detect and image neurotransmitters released upon exocytosis.

SUMMARY OF THE INVENTION

The present invention provides a series of pH-sensitive fluorescent sensors for imaging exocytosis of the neurotransmitters. The inventive sensor is dual-analyte chemosensor that selectively labels primary amine neurotransmitters found at high concentrations within vesicles (e.g., glutamate, norepinephrine, and dopamine) and concomitantly allows for direct visualization of only active neurotransmitters released upon exocytosis by capitalizing on the pH gradient between the vesicle and the synaptic cleft.

One embodiment of the present invention is directed to a fluorescence sensing compound for detecting and visualizing a synaptic release of one or more primary amine neurotransmitters, the fluorescence sensing compound having the following formula:

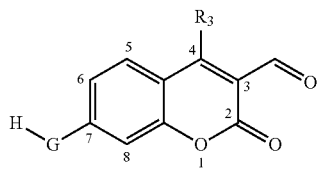

wherein:
the -GH group at the C7-position is an electron-donor that confers an internal charge transfer mechanism to the compound upon deprotonation, which occurs at a pH that is greater than 5 and less than 7.4, and wherein the -GH group is selected from the group consisting of sulfamidyl, sulfonamidyl, hydroxyl, amidyl, arylamino, and alkylamino;

the aldehyde group at the C3-position is an electron-acceptor and enables iminium-ion formation with said primary neurotransmitter(s);

$R_3$ is selected from the group consisting of hydrogen, alkyl, alkylene, aryl, and cycloakyl; and the fluorescence sensing compound has a p$K_a$ is in a range of about 6.0 to about 7.4.

Another embodiment of the present invention is directed to a the foregoing sensing compound, wherein the -GH group is sulfamidyl having the following formula:

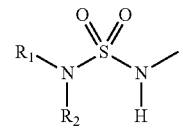

wherein $R_1$ and $R_2$ are each independently selected from the group consisting of hydrogen, alkyl, alkylene, aryl, and cycloakyl.

Another embodiment of the present invention is directed to the fluorescence sensing compound of the immediately preceding paragraph, wherein, $R_1$ is alkyl, $R_2$ is alkyl, and $R_3$ is aryl.

Another embodiment of the present invention is directed to the fluorescence sensing compound of the immediately preceding paragraph, wherein $R_1$ is methyl, $R_2$ is methyl, and $R_3$ is phenyl.

Another embodiment of the present invention is directed to the aforementioned fluorescence sensing compound, wherein the -GH group is a sulfonamidyl having the following formula:

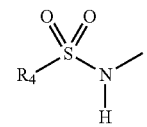

wherein $R_4$ is selected from the group consisting of hydrogen, alkyl, alkylene, aryl, and cycloakyl.

Another embodiment of the present invention is directed to the fluorescence sensing compound of the immediately preceding paragraph, wherein $R_4$ is an alkyl or an aryl, and $R_3$ is aryl.

Another embodiment of the present invention is directed to the fluorescence sensing compound of the immediately preceding paragraph, wherein $R_4$ is methyl or thiophene moiety, and $R_3$ is phenyl.

Another embodiment of the present invention is directed to a fluorescence sensing compound for detecting and visualizing a synaptic release of one or more primary amine neurotransmitters having the following formula:

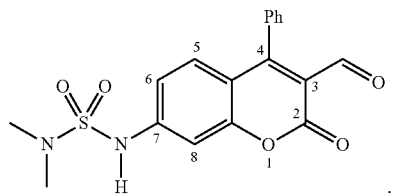 [SMILES: CN(C)S(=O)(=O)Nc1ccc2c(-c3ccccc3)c(C=O)c(=O)oc2c1]

Another embodiment of the present invention is directed to a method of detecting one or more primary neurotransmitters released during exocytosis, the method comprising:
a. contacting chromaffin cells with one of the aforementioned fluorescence sensing compounds; wherein the fluorescence sensing compound enters vesicles of the chromaffin cells and binds to the primary neurotransmitter(s) in the vesicles; and
b. detecting the presence of absence of fluorescence, wherein the presence of fluorescence indicates the release of the primary amine neurotransmitters bound to the fluorescence sensing compound from the vesicles into clefts of the chromaffin cells during exocytosis.

DETAILED DESCRIPTION OF THE INVENTION

Unless otherwise defined, all technical and scientific terms used herein have the same meaning as commonly understood by one of ordinary skill in the art to which this invention belongs. Throughout the specification and claims, a given chemical formula or name shall encompass all optical and stereoisomers as well as racemic mixtures where such isomers and mixtures exist.

In one embodiment, the present invention is directed to pH-sensitive fluorescent sensors useful for imaging exocytosis of the neurotransmitters. The inventive sensors are designed to contain an electron donor at the coumarin 7-position and an electron acceptor at the 3-position,

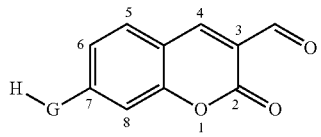

wherein the electron-acceptor at the 3-position enables iminium-ion formation with a primary amine, and the electron-donor motif at the 7-position confers an internal charge transfer (ICT) mechanism whereby upon deprotonation, the internal charge transfers across the molecule.

Figure 1:
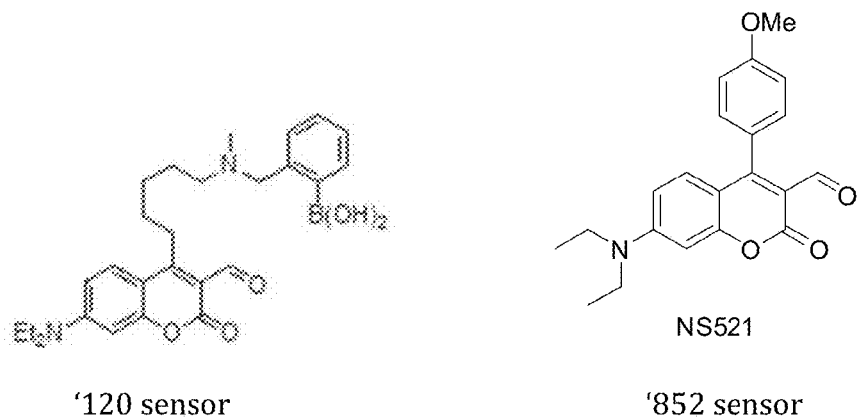
FIG. 1 illustrates the chemical structures of coumarin-aldehyde based fluorescent disclosed in U.S. Pat. No. 7,977,120 and International Application No. PCT/US2014/31490.
Figure 2:
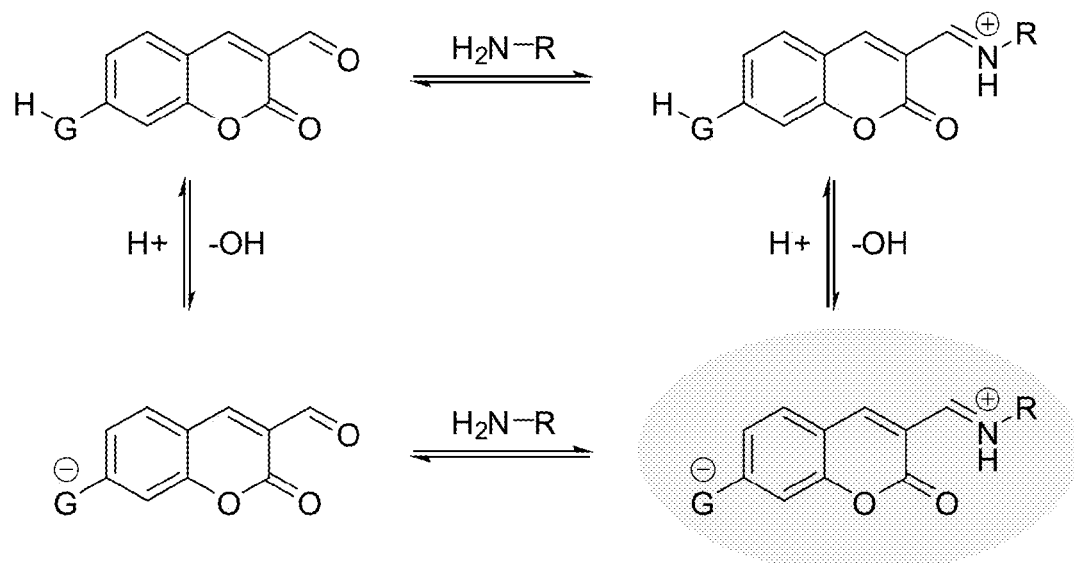
FIG. 2 is a schematic illustration of protonation states of the bound and unbound sensor of the present invention.

FIG. 2 illustrates the dual-analyte functions of inventive sensors when encountering a primary amine upon a pH change in the environment. As shown in FIG. 2, deprotonation of the 7-position (G) confers an increase in fluorescence response at 517 nm, while binding of the sensor's aldehyde (3-position) to a primary amine further enhances the charge transfer by forming an iminium ion, which is a better electron acceptor given that it has a formal positive charge. Both the deprotonation of the donor group and the binding to the primary amine concurrently have been observed to achieve the maximal charge transfer thereby tending to afford a maximal fluorescence turn-on response. The dual-analyte design strategy of the inventive sensors allow for direct detection and imaging of released neurotransmitters during exocytosis and is believed to represent one of the first molecular logic gate-based design strategies for biological purposes.

Figure 3:
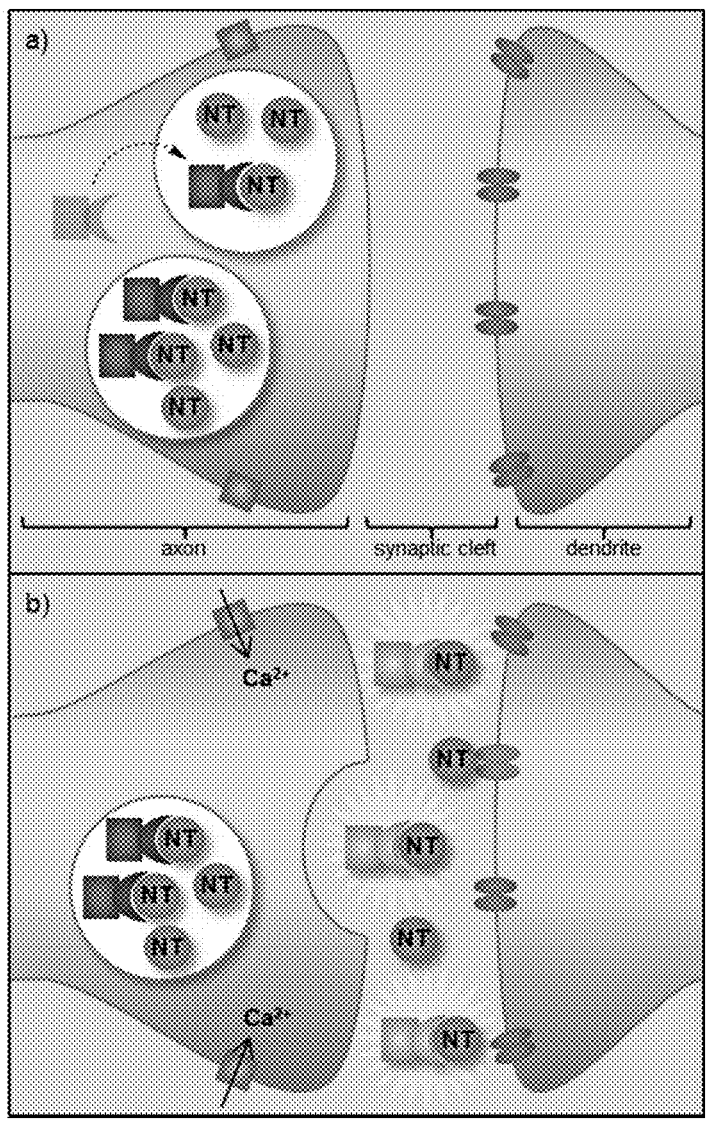
FIG. 3 is a schematic illustration of a sensing process involving a sensor of the present invention during exocytosis.

FIG. 3 is a schematic illustration of the inventive sensor's sensing process during exocytosis. As shown in FIG. 3, the inventive sensor enters the vesicle and selectively binds to primary amine neurotransmitters at high concentrations, yet remain fluorescently "off" due to the acidic environment. Formation of a positively charged complex causes the bound sensor to become trapped within the vesicle, encouraging sensor accumulation. Upon exocytosis, the bound sensor complex is secreted into the synaptic cleft, where the change in environmental pH deprotonates the sensor and switches the fluorescence "on" for only the released sensor in its bound state.

The inventive sensors are designed to exploit the pH gradient between the synaptic vesicle (pH~5) and the synaptic cleft (pH 7.4), which requires the pKa of the fluorophore to be around 6.0-6.3. Though other functional G groups may be selected, the sulfonamide functional group with a pKa around 6 is chosen to be the reversible recognition motif. Thus, the present invention provides a coumarin-aldehyde-and-sulfonamide-moiety-based fluorescence sensing compound, of the Formula (I):

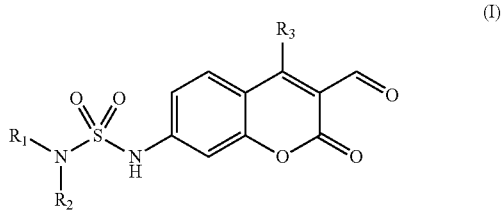

wherein $R_1$, $R_2$, $R_3$ are each independently hydrogen, alkyl, alkylene, aryl, or cycloalkyl.

By "independently," the skilled artisan will appreciate that each and every group may be selected from the entire list set forth as possible selections without regard to the selections of other groups having the same or different appellations.

As used herein the term "alkyl" refers to C1-10 inclusive, linear, branched, or cyclic, saturated or unsaturated (i.e., alkenyl and alkynyl) hydrocarbon chains. The alkyl group can be optionally substituted with one or more alkyl group substituents which can be the same or different, where "alkyl group substituent" includes alkyl, halo, arylamino, acyl, hydroxyl, aryloxy, alkoxyl, alkylthio, arylthio, aralkyloxy, aralkylthio, carboxy, alkoxycarbonyl, oxo and cycloalkyl. There can be optionally inserted along the alkyl chain one or more oxygen, sulfur or substituted nitrogen atoms, wherein the nitrogen substituent is hydrogen, lower alkyl (also referred to herein as "alkylaminoalkyl"), or aryl. "Branched" refers to an alkyl group in which a lower alkyl group, such as methyl, ethyl or propyl, is attached to linear alkyl chain.

"Aryl" refers to an aromatic substituent that may be a single ring or multiple rings that are fused together, linked covalently, or linked to a common group such as an ethylene, methylene or oxy moiety. The aromatic rings of the aryl group may each and optionally contain heteroatoms. The aryl group can be optionally substituted with one or more aryl group substituents which can be the same or different, where "aryl group substituent" includes alkyl, aryl, arylalkyl, hydroxy, alkoxyl, aryloxy, arylalkoxyl, carboxy, acyl, halo, nitro, alkoxycarbonyl, aryloxycarbonyl, arylalkoxycarbonyl, acyloxyl, acylamino, aroylamino, carbamoyl, alkylcarbamoyl, dialkylcarbamoyl, arylthio, alkylthio, alkylene and —NRR', where R and R' can be each independently hydrogen, alkyl, aryl and aralkyl.

As used herein, the terms "substituted alkyl" and "substituted aryl" include alkyl and aryl groups, as defined herein, in which one or more atoms or functional groups of the aryl or alkyl group are replaced with another atom or functional group, including for example, halogen, aryl, alkyl, alkoxyl, hydroxyl, nitro, amino, alkylamino, dialkylamino, sulfate, and mercapto.

"Cyclic" and "cycloalkyl" refer to a non-aromatic mono- or multicyclic ring system of about 3 to about 10 carbon atoms. The cycloalkyl group can be optionally partially unsaturated. The cycloalkyl group can be also optionally substituted with an alkyl group substituent as defined herein, ox and/or alkylene. There can be optionally inserted along the cyclic alkyl chain one or more oxygen, sulfur or substituted nitrogen atoms, wherein the nitrogen substituent is hydrogen, lower alkyl, or aryl, thus providing a heterocyclic group.

"Alkylene" refers to a straight or branched bivalent aliphatic hydrocarbon group having from 1 to about 10 carbon atoms. The alkylene group can be straight, branched or cyclic. The alkylene group can be also optionally unsaturated and/or substituted with one or more "alkyl group substituents." There can be optionally inserted along the alkylene group one or more oxygen, sulfur or substituted nitrogen atoms, wherein the nitrogen substituent is alkyl as previously described.

Furthermore, one inventive sensor, ES517,

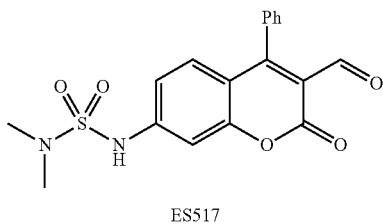 [SMILES: CN(C)S(=O)(=O)Nc1ccc2c(-c3ccccc3)c(C=O)c(=O)oc2c1]

Figure 4:
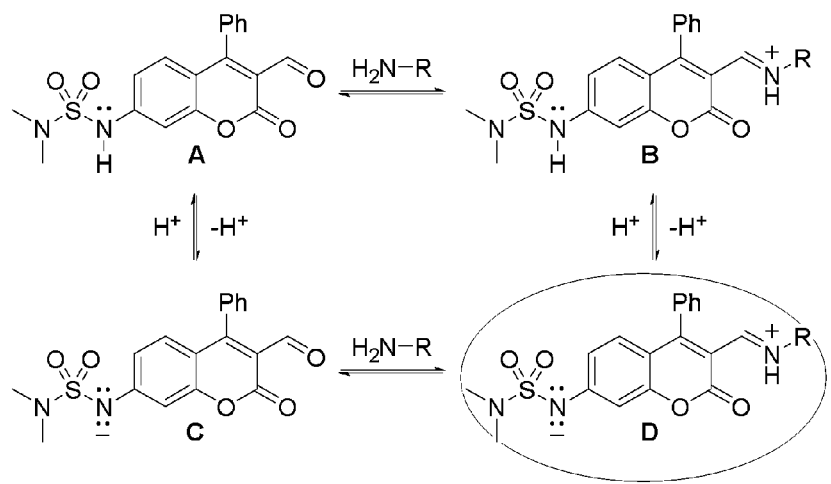
FIG. 4 is a schematic illustration of the ES517's dual-analyte function in vesicle and upon exocytosis.

ES517 was selected to demonstrate the dual-analyte sensing process. FIG. 4 further illustrates the ES517 dual-analyte function in vesicles and upon exocytosis. As shown in FIG. 4, in the cytosol, ES517 (A) exists largely in the deprotonated form (C) due to the neutral pH and relatively low concentration of amines. Both forms A and C have weak fluorescence as they lack the iminium ion as a strong acceptor regardless of being protonated (A) or deprotonated (C). When ES517 enters the vesicle, it binds to the neurotransmitter due to its high concentration producing the iminium ion B. Form B has marginal electron transfer and weak fluorescence since the protonated sulfamide is a weak donor. Upon exocytosis, the bound complex enters the synaptic cleft, becomes deprotonated (structure D), and produces a marked fluorescence increase due to the enhanced ICT.

Figure 5:
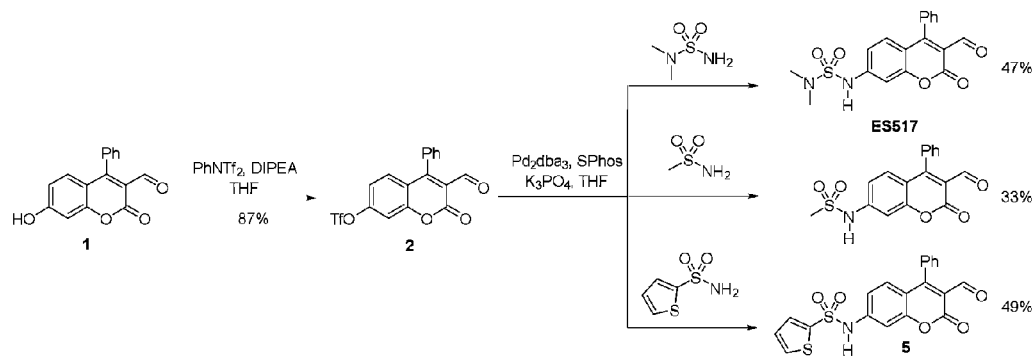
FIG. 5 illustrates a schematic synthesis of sensors of the present invention.

The invention further provides an exemplary synthesis scheme for the inventive sensor. FIG. 5 illustrates the schematic synthesis of inventive sensor. As shown in FIG. 5, a series of sensors were synthesized from compound 1, and triflation of the phenol of compound 1 gave compound 2 which underwent a Buchwald-Hartwig coupling reaction with various aliphatic and aromatic sulfonamides to give the final products. The synthesis allows for sensor pKa optimization through the coupling of various pH-sensitive sulfonamides which in turn, augments the fluorescence turn-on response to exocytotic conditions. This broadens the tools for visualizing neurotransmission to small molecular sensors that can be easily tailored to fit specific experiment parameters.

The spectroscopic properties of several exemplary inventive sensors have been examined, along with the starting compound 1, as 7-hydroxycoumarins are well known for their pH-sensitivity. First, the acidity of the sensors was discerned by performing pH titrations where aliquots of aqueous HCl were added to a buffered solution of the sensor and the absorbance and fluorescence were monitored. The pKa of the pH-sensitive unit is related to the donating ability of the sulfonamide substituent. ES517 has a dimethylamino-substituent on the sulfonamide which is the best electron-donor into the sulfonyl motif. This makes deprotonation of the N—H proton located at the 7-position of the coumarin core the least favorable and therefore the least acidic. The pH and fluorescence intensity data were fit to a pH isotherm and the pKa was determined to be 6.3. As the donating ability of the sulfonamide substituent into the sulfonyl motif worsened, the acidity of the N—H proton located at the 7-position of the coumarin core increased. The aromatic substituents are the least electron donating substituents into the sulfonyl motif which explains the greater acidity. By using a single coupling reaction, the pKa of the sensor may be tuned to fit the parameters of the experiment.

Next, the sensor was saturated with 300 mM glutamate in order to mimic vesicular conditions. The fluorescence intensity of the bound complex was then monitored between the pH values of 5 and 7.4, the acidities associated with the synaptic vesicle and synaptic cleft, respectively. An excitation wavelength of 488 nm was used because it is far enough to the red to ensure that only the bound, deprotonated sensor was excited. It is also a common wavelength used in fluorescence microscopy cell studies. The fluorescence intensity increased for all sensors upon basification from pH 5 to 7.4, however the sensors with the highest pKa values gave the greatest enhancements.

Table 1 summarizes the spectroscopic properties of the tested compounds in pH varying environments, mimicking the vesicular and synaptic cleft conditions. The inventive sensors were observed to both bind to the primary amine neurotransmitter (glutamate) and exhibit a notable fluorescence enhancements between the pH values of 5 (synaptic vesicle) and 7.4 (synaptic cleft).

TABLE 1

Spectroscopic properties of unbound sensors.

| Sensor | $pK_a$ | $\lambda_{max}$ (GH/G-) | $\lambda_{em}$ (ex: 488 nm) | $I_{pH7.4}/I_{pH 5}{}^a$ |
|---|---|---|---|---|
| (ES517 structure) | 6.3 | 368/419 | 498 | 12 |

TABLE 1-continued

Spectroscopic properties of unbound sensors.

| Sensor | $pK_a$ | $\lambda_{max}$ (GH/G-) | $\lambda_{em}$ (ex: 488 nm) | $I_{pH7.4}/I_{pH5}$[a] |
|---|---|---|---|---|
| [Ph-substituted coumarin with methanesulfonamide] | 5.9 | 365/420 | 489 | 5.5 |
| [Ph-substituted coumarin with thiophenesulfonamide] | 5.2 | 366/416 | 494 | 2.5 |
| [Ph-substituted 7-hydroxycoumarin] | 5.8 | 368/420 | 468 | 3.3 |

[a]Sensor saturated with 0.3M glutamate and intensities monitored at pH 5.0 and 7.4

The ES517 was further analyzed for binding and spectroscopic properties with the common neurotransmitters other than glutamate released upon exocytosis. Table 2 summarizes the results with various neurotransmitters, which shows that all non-aromatic neurotransmitters produced large fluorescence increases upon pH change from 5.0 to 7.4. Whereas, the catecholamines gave smaller, but still significant fluorescence increases, and serotonin was unique in that it gave little fluorescence change. The aromatic neurotransmitters dampened the fluorescence turn-on response of the inventive sensors due to the electron-rich nature of catecholamines (norepinephrine and dopamine) and indoleamines (serotonin).

TABLE 2

Binding and spectroscopic properties of ES517 with various primary amine neurotransmitters.

| Neurotransmitter[a] | $K_a$ ($M^{-1}$) | $I_{sat}/I_0$[b] | $I_{pH\,7.4}/I_{pH\,5}$[c] |
|---|---|---|---|
| glutamate | 8.6 | 12 | 12[d] |
| GABA | 8.3 | 27 | 11[d] |
| glycine | 9.2 | 25 | 10[d] |
| norepinephrine | 49 | 14 | 5.3[e] |
| dopamine | 55 | 10 | 5.5[e] |
| serotonin | 54 | 0.5 | 1.5[e] |

[a]Binding studies of ES517 (20 μM) with saturating amounts of analyte in buffered conditions (50 mM bis-tris propane, 50 mM $Na_2S_2O_3$, 1% DMSO, pH 7.4) with ±10% error based on triplicate titration.
[b]Fluorescence enhancement upon binding analyte at pH 7.4 ($I_{sat}$ taken from the theoretical max of the binding isotherm). $\lambda_{em}$ = 517 nm.
[c]Ratio of fluorescence at pH 7.4 vs. 5.0 of ES517 (20 μM) saturated with analyte.
[d]Saturated with 300 mM analyte.
[e]Saturated with 100 mM analyte.

EXAMPLES

Example 1: Synthesis of ES517

Compound 1 (465 mg, 1.746 mmol) and N-phenyltriflimide (686 mg, 1.921 mmol) were combined in a round bottom flask. THF (24 mL) was added and then DIPEA was added dropwise (0.38 mL, 2.270 mmol). The mixture stirred at ambient temperature for 3 h followed by removal of the solvent in vacuo. The residue was purified by chromatography (95:5 $CH_2Cl_2$/EtOAc) to yield Compound 2 (607.2 mg, 87%) as a golden oil: $^1$H NMR (500 MHz, $CDCl_3$) δ 9.95 (s, 1H), 7.56-7.62 (m, 3H), 7.33-7.37 (m, 2H), 7.29-7.32 (m, 2H), 7.16 (dd, 1H, J=9.0, 2.5 Hz); $^{13}$C NMR (125 MHz, $CDCl_3$) δ 187.5, 159.5, 157.1, 155.0, 152.6, 131.4, 130.8, 130.3, 129.0, 128.4, 119.9, 119.7 (q, C—F, J=40 Hz), 118.0, 117.3, 110.6; IR (neat, $cm^{-1}$) 1765, 1605, 1552, 1422, 1364, 1217, 1136, 1107, 980; HRMS calculated for $C_{17}H_9F_3O_6SNa$ (M+Na$^+$): 420.9964. Found: 420.9961.

Compound 2 (123 mg, 0.309 mmol) was combined with N,N-dimethylsulfamide (42 mg, 0.340 mmol), $Pd_2dba_3$ (14 mg, 0.015 mmol), SPhos (18 mg, 0.046 mmol), and $K_3PO_4$ (132 mg, 0.618 mmol) in a round bottom flask and degassed for 20 min. Dry degassed THF was added and the mixture was purged with $N_2$ for 30 min followed by heating at 55° C. for 24 h. The solvent was evaporated with a stream of $N_2$, the crude product taken up in water (pH 5), and extracted with EtOAc (15 mL×3). Purification by chromatography (95:5 $CH_2Cl_2$/EtOAc) gave ES517 (54 mg, 47%) as a yellow solid (mp 195 C): $^1$H NMR (500 MHz, $CDCl_3$) δ 9.91 (s, 1H), 7.52-7.58 (m, 3H), 7.27-7.31 (m, 2H), 7.19 (d, 1H, J=2.0 Hz), 7.15 (d, 1H, J=9.0 Hz), 6.93 (dd, 1H, J=9.0, 2.0 Hz), 2.93 (s, 6H); $^{13}$C NMR (125 MHz, $CDCl_3$) δ 188.2, 161.5, 158.4, 155.9, 144.1, 131.6, 130.8, 129.9, 128.8, 128.4, 116.9, 115.1, 114.5, 104.8, 38.1; IR (KBr, $cm^{-1}$)

3260, 1732, 1610, 1528, 1377, 1140; HRMS calculated for $C_{18}H_{16}N_2O_5SNa$ (M+Na$^+$): 395.0672. Found: 395.0670.

Example 2: Spectroscopic Property Studies of ES517

Figure 6:
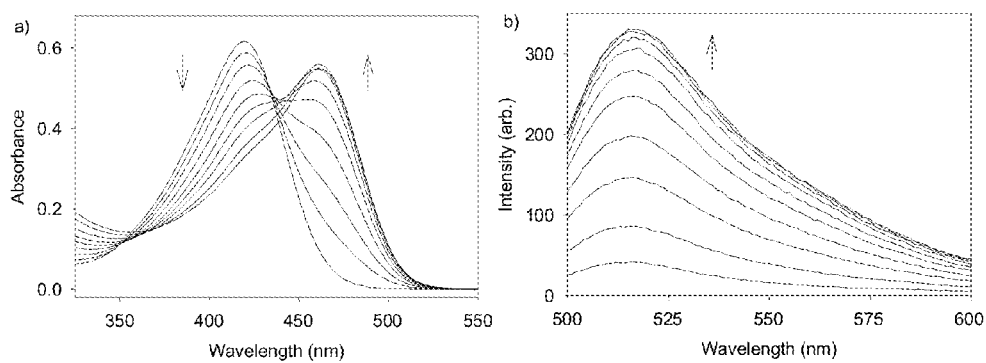
FIG. 6 illustrates the initial binding studies of ES517 with glutamate.

FIG. 6 shows results of initial binding studies performed by titrating ES517 with glutamate and exciting at 488 nm, a region that is sufficiently red to prohibit absorbance and subsequent emission from the unbound sensor. A 12-fold fluorescence enhancement was obtained upon binding to glutamate though with a low binding constant ($K_a$=8.6 M$^{-1}$). While low, this binding constant is believed to be preferred for reversible binding due to the high millimolar concentration of glutamate in a vesicle (~300 mM).

Figure 7:
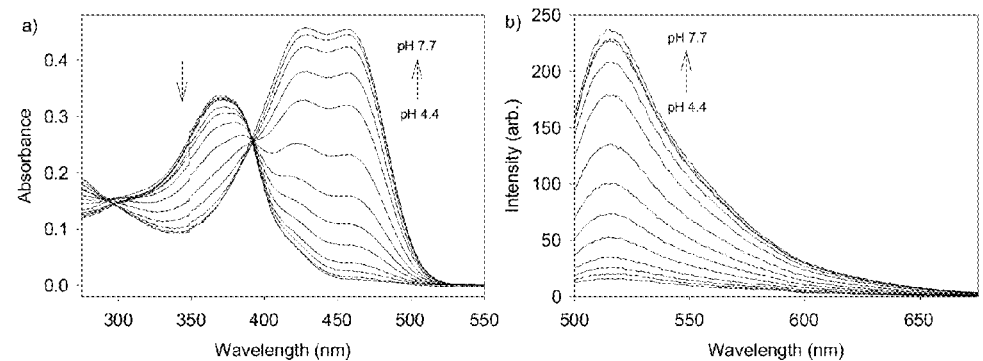
FIG. 7 illustrates the pKa, and fluorescence enhancement at 517 nm of the ES517 sensor bound with glutamate.

FIG. 7 shows the tests of the pKa of the bound sensor. ES517 was saturated with glutamate and the spectroscopic properties measured over a wide pH range. The protonated form of the bound sensor (FIG. 4, structure B) absorbed at 368 nm. Upon deprotonation, two bands were observed at 428 and 458 nm. The 428 nm band was assigned to the unbound deprotonated form of the sensor (structure C). The 458 nm band therefore represents the bound, deprotonated sensor (structure D). The plot of pH vs. intensity was fit to a pH isotherm and the pKa determined to be 6.3.

While the invention has been described in connection with specific embodiments thereof, it will be understood that the inventive method is capable of further modifications. This patent application is intended to cover any variations, uses, or adaptations of the invention following, in general, the principles of the invention and including such departures from the present disclosure as come within known or customary practice within the art to which the invention pertains and as may be applied to the essential features herein before set forth and as follows in scope of the appended claims.

What is claimed is:

1. A fluorescence sensing compound for detecting and visualizing a synaptic release of one or more primary amine neurotransmitters, the fluorescence sensing compound having the following formula:

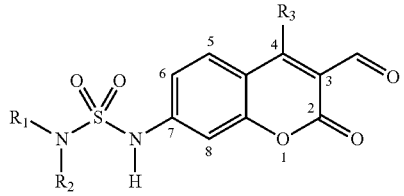

wherein:
the sulfamidyl group at the C7-position is an electron-donor that confers an internal charge transfer mechanism to the compound upon deprotonation, which occurs at a pH that is between that of a synaptic vesicle and that of a synaptic cleft;
the aldehyde group at the C3-position is an electron-acceptor and enables an iminium-ion formation with said primary amine neurotransmitter(s);
$R_1$ and $R_2$ are each independently selected from the group consisting of hydrogen, alkyl, alkylene, aryl, and cycloakyl;
$R_3$ is selected from the group consisting of hydrogen, alkyl, alkylene, aryl, and cycloakyl; and
the fluorescence sensing compound has a p$K_a$ that is in a range of 6.0 to 7.4.

2. The fluorescence sensing compound of claim 1, wherein $R_1$ is alkyl, $R_2$ is alkyl, and $R_3$ is aryl.

3. The fluorescence sensing compound of claim 2, wherein $R_1$ is methyl, $R_2$ is methyl, and $R_3$ is phenyl.

4. A method of detecting one or more primary neurotransmitters released during exocytosis, the method comprising:
a. contacting chromaffin or neuron cells with a fluorescence sensing compound; wherein the fluorescence sensing compound enters vesicles of the cells and binds to the primary neurotransmitter(s) in the vesicles;
b. detecting the presence of absence of fluorescence, wherein the presence of fluorescence indicates the release of the primary amine neurotransmitters bound to the fluorescence sensing compound from the vesicles into clefts of the cells during exocytosis; and
wherein the fluorescence sensing compound has following formula:

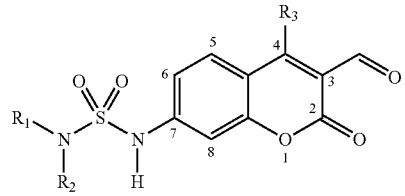

wherein:
the sulfamidyl group at the C7-position is an electron-donor that confers an internal charge transfer mechanism to the compound upon deprotonation, which occurs at a pH that is between that of a synaptic vesicle and that of a synaptic cleft;
the aldehyde group at the C3-position is an electron-acceptor and enables an iminium-ion formation with said primary amine neurotransmitter(s);
$R_1$ and $R_2$ are each independently selected from the group consisting of hydrogen, alkyl, alkylene, aryl, and cycloakyl;
$R_3$ is selected from the group consisting of hydrogen, alkyl, alkylene, aryl, and cycloakyl; and
the fluorescence sensing compound has a p$K_a$ that is in a range of 6.0 to 7.4.

5. The method of claim 4, wherein $R_1$ is alkyl, $R_2$ is alkyl, and $R_3$ is aryl.

6. The method of claim 5, wherein $R_1$ is methyl, $R_2$ is methyl, and $R_3$ is phenyl.

7. The fluorescence sensing compound of claim 1, wherein the fluorescence sensing compound has a p$K_a$ is in a range of 6.0 to 6.3.

* * * * *